(12) United States Patent
Kent et al.

(10) Patent No.: US 10,376,689 B2
(45) Date of Patent: Aug. 13, 2019

(54) LEADS FOR EXTRAFORAMINAL STIMULATION OF DORSAL ROOTS AND DORSAL ROOT GANGLIA AND RELATED METHODS

(71) Applicant: Pacesetter, Inc., Sunnyvale, CA (US)

(72) Inventors: Alexander Kent, Mountain View, CA (US); William Cusack, Mountain View, CA (US); Xiaoyi Min, Camarillo, CA (US); Gene A. Bornzin, Simi Valley, CA (US)

(73) Assignee: PACESETTER, INC., Sylmar, CA (US)

( * ) Notice: Subject to any disclaimer, the term of this patent is extended or adjusted under 35 U.S.C. 154(b) by 31 days.

(21) Appl. No.: 15/386,981

(22) Filed: Dec. 21, 2016

(65) Prior Publication Data

US 2018/0169405 A1   Jun. 21, 2018

(51) Int. Cl.
*A61N 1/05* (2006.01)
*A61N 1/36* (2006.01)
*A61N 1/06* (2006.01)

(52) U.S. Cl.
CPC ....... *A61N 1/0551* (2013.01); *A61N 1/36071* (2013.01); *A61N 1/0504* (2013.01); *A61N 1/0553* (2013.01); *A61N 1/0558* (2013.01); *A61N 1/06* (2013.01); *A61N 1/36171* (2013.01); *A61N 1/36175* (2013.01)

(58) Field of Classification Search
CPC ............................. A61N 1/0551; A61N 1/0504
USPC .......................................................... 607/46
See application file for complete search history.

(56) References Cited

U.S. PATENT DOCUMENTS

| | | | | |
|---|---|---|---|---|
| 5,330,515 | A | * | 7/1994 | Rutecki .............. A61N 1/36071 607/46 |
| 5,843,141 | A | * | 12/1998 | Bischoff .............. A61N 1/3752 607/37 |
| 7,450,993 | B2 | | 11/2008 | Kim et al. |
| 2013/0085548 | A1 | | 4/2013 | Mironer |

* cited by examiner

*Primary Examiner* — Nadia A Mahmood

(57) ABSTRACT

The present disclosure generally relates to extraforaminal electrical stimulation systems and leads for electrical stimulation of the dorsal root and dorsal root ganglion (DRG), minimally invasive implantation methods therefore, and related methods of providing extraforaminal electrical stimulation of the dorsal root and DRG for the treatment of a medical condition. In accordance with certain aspects, the extraforaminal electrical stimulation leads and methods are particularly suited for stimulation of dorsal roots and DRG of the cervical and thoracic spine.

20 Claims, 7 Drawing Sheets

LEADS FOR EXTRAFORAMINAL STIMULATION OF DORSAL ROOTS AND DORSAL ROOT GANGLIA AND RELATED METHODS

FIELD OF THE INVENTION

Aspects of the present invention relate to medical devices and methods. More specifically, the present invention relates to leads surgically implantable in a patient for electrical stimulation of nerve or tissue.

BACKGROUND OF THE INVENTION

Medical conditions may be treated through the application of electrical stimulation. For example, Spinal Cord Stimulation (SCS) involves driving an electrical current into particular regions of the spinal cord to induce analgesia in persons with chronic pain. SCS may also generate paresthesia, which is a subjective sensation of numbness or tingling in a region of the body associated with the stimulated spinal cord region. Paresthesia can mask the transmission of chronic pain sensations from the afflicted regions of the body to the brain, thereby providing pain relief to the patient.

Additionally, electrical stimulation of the dorsal root and dorsal root ganglion (DRG) is often used at the lumbar spinal levels for the treatment of chronic pain of the back and lower limbs. In typical treatment, each lead is inserted through the skin, fat, and muscle layers into the epidural space above the spinal cord. The leads are then steered outwards through the neural foramen while targeting an epidural placement on the DRG corresponding to the region of pain. This procedure is typically performed with up to four lead placements in the lumbar spinal levels.

In order to target pain in the neck and upper limbs, placement of epidural leads near DRG at the cervical levels is required. However, placing leads at this anatomical location is substantially more difficult due to several factors. Firstly, the spinal foramen opening at the cervical layer is narrower than that of the lumbar/thoracic levels, thus increasing the risk of tissue damage during electrode placement or migration. Secondly, the cervical region is typically comprised of less soft tissue, and thus provides complication to the surgical approach, including decreased opportunities for lead fixation. Finally, due to the relatively high amount of motion of the cervical spine relative to the lumbar/thoracic spine, there is a higher risk of lead migration, neural tissue damage, and loss of therapeutic efficacy.

As such, there is a need for paddle leads deployable from a minimally invasive surgical approach. It is with these observations in mind, among others, that various aspects of the present disclosure were conceived and developed.

As such, there is a need for improved devices and techniques for electrical stimulation of the dorsal root and DRG, particularly in the cervical and/or thoracic region. The present disclosure addresses these and other needs.

BRIEF SUMMARY OF THE INVENTION

In certain aspects, implementations described and claimed herein address the foregoing problems, among others, by providing dorsal root and dorsal root ganglion (DRG) stimulation leads and methods of implanting the same.

In certain aspects, the present disclosure generally relates to extraforaminal electrical stimulation systems and leads for electrical stimulation of the dorsal root and DRG from the extraforaminal area of the spine.

In certain embodiments, the extraforaminal electrical stimulation lead for the extraforaminal electrical stimulation of at least one dorsal root and DRG may generally comprise a lead body formed of an electrically insulative material; at least one conductive electrode contact positioned in at least one surface of the lead body to provide electrical stimulation upon application of electrical current to the lead; at least one conductive member configured to connect the at least one conductive electrode contact to a power source; wherein the lead body is sized and shaped so as to facilitate implantation in the extraforaminal area in proximity to at least one dorsal root and DRG.

In other aspects, minimally invasive methods for the implantation of electrical stimulation leads of the disclosure into an extraforaminal area of a patient are provided. The methods generally comprise, providing a small incision through the dermis of a patient near a target region of the spine of a patient for placement of an extraforaminal electrical stimulation lead; implanting an extraforaminal electrical stimulation lead in the subcutaneous fat layer of the patient, between the skin and musculature, in an extraforaminal area of the target region of the spine of the patient in proximity of at least one dorsal root and DRG; and optionally suturing the extraforaminal electrical stimulation lead to anchor the lead in place.

In yet other aspects, methods of providing extraforaminal electrical stimulation of the dorsal root and DRG for the treatment of a medical condition are provided. In certain embodiments, the method of providing extraforaminal electrical stimulation to a dorsal root and DRG to provide analgesia to a patient in need thereof comprises delivering electrical current from at least one electrical stimulation lead implanted in an extraforaminal area of the spine of a patient in proximity to at least one dorsal root and DRG in a target region of the patient to thereby provide analgesia to the patient.

In accordance with certain aspects, the extraforaminal electrical stimulation leads and methods are particularly suited for stimulation of dorsal roots and DRG of the cervical and/or thoracic spine. In other aspects, extraforaminal electrical stimulation leads and methods are particularly suited to provide unidirectional electrical stimulation upon application of electrical current to the lead.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

Although the following figures and description illustrate specific embodiments and examples, the skilled artisan will appreciate that various changes and modifications may be made without departing from the spirit and scope of the disclosure.

Additional embodiments and features are set forth in part in the description that follows, and will become apparent to those skilled in the art upon reading of the specification. A further understanding of the nature and advantages of the present disclosure can be realized by reference to the remaining portions of the specification and the drawings, which forms a part of this disclosure.

DETAILED DESCRIPTION

Reference will now be made in detail to representative embodiments described herein and illustrated in the accompanying drawings. It should be understood that the following descriptions are not intended to limit the disclosure to one preferred embodiment. To the contrary, it is intended to cover alternatives, modifications, and equivalents as can be included within the spirit and scope of the described embodiments as defined by the appended claims.

In certain aspects, the present disclosure generally relates to extraforaminal electrical stimulation systems and leads for electrical stimulation of the dorsal root and dorsal root ganglion (DRG) from the extraforaminal area of the spine. Other aspects relate to minimally invasive implantation methods therefore, and related methods of providing extraforaminal electrical stimulation of the dorsal root and DRG for the treatment of a medical condition. In accordance with certain aspects, the extraforaminal electrical stimulation leads and methods are particularly suited for stimulation of dorsal roots and DRG of the cervical and/or thoracic spine.

Figure 1:
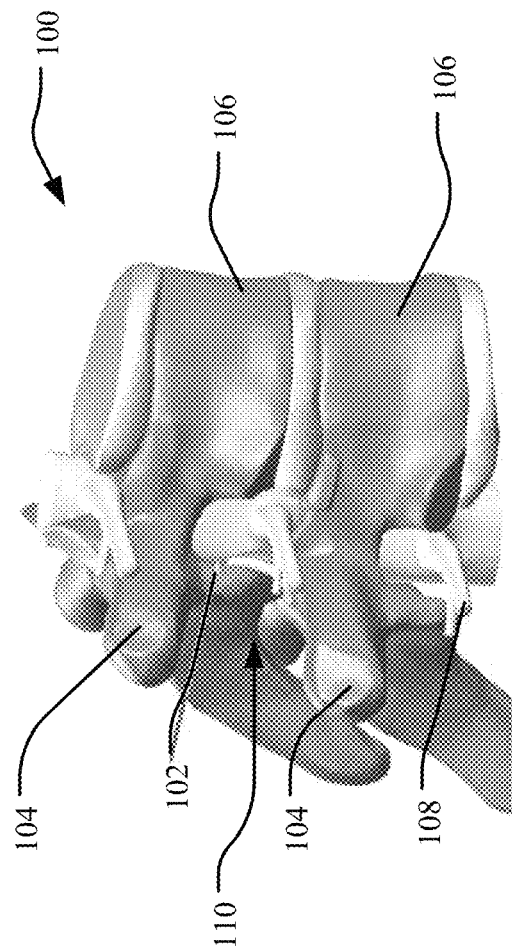
FIG. 1 is an illustration of structures within the spinal column, including the spinal foramen.

In accordance with certain aspects of the disclosure, to begin a detailed description of extraforaminal electrical stimulation systems and related methods for the treatment of a patient for a medical condition, such as chronic pain, through the application of electrical stimulation to a target region in the extraforaminal area, reference is made to FIG. 1. In the vertebrate spinal column 100 of a patient, the spinal foramen 102 is formed between adjacent vertebrae 106, which have spinous process 104 projecting therefrom and providing a point of attachment for muscles and ligaments of the patient. The neural foramen 102 provides the opening through which spinal nerve roots 108 travel and exit to other parts of the body. The extraforaminal area 110 is located adjacent the neural foramen 102.

Figure 2:
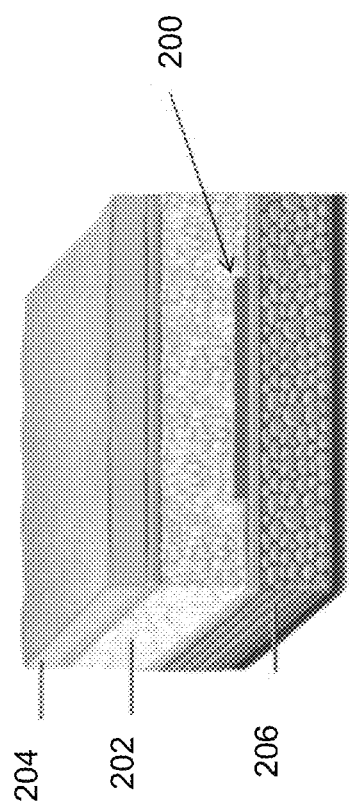
FIG. 2 is a cross-sectional view showing the location of a subdermal patch lead following implantation in accordance with an embodiment of the disclosure, within the subcutaneous fat layer between the skin and muscle.

In certain aspects, an extraforaminal electrical stimulation lead of the disclosure may be implanted subcutaneously in the extraforaminal area in proximity to the dorsal root and DRG in the target region of interest to provide electrical stimulation to the dorsal root and DRG, rather than through the narrow spinal foramen. For instance, with reference to FIG. 2, an extraforaminal electrical stimulation lead 200 may be implanted in the subcutaneous fat layer 202 between the skin 204 and musculature 206. Without intending to be limited, because the lead does not pass through muscle, movement of the spine will impart less relative motion to the lead. As such, there is a reduced risk of lead migration, and a reduced need for explicit fixation of the lead.

In certain embodiments, methods for the minimally invasive implantation of an extraforaminal electrical stimulation lead into a patient in need thereof are provided comprising implanting a lead into a subdermal layer of the patient in an extraforaminal area of a target region of interest in proximity to one or more dorsal roots and DRGs to thereby provide electrical stimulation to the dorsal roots and DRGs upon application of electrical current to the lead.

Figure 3:
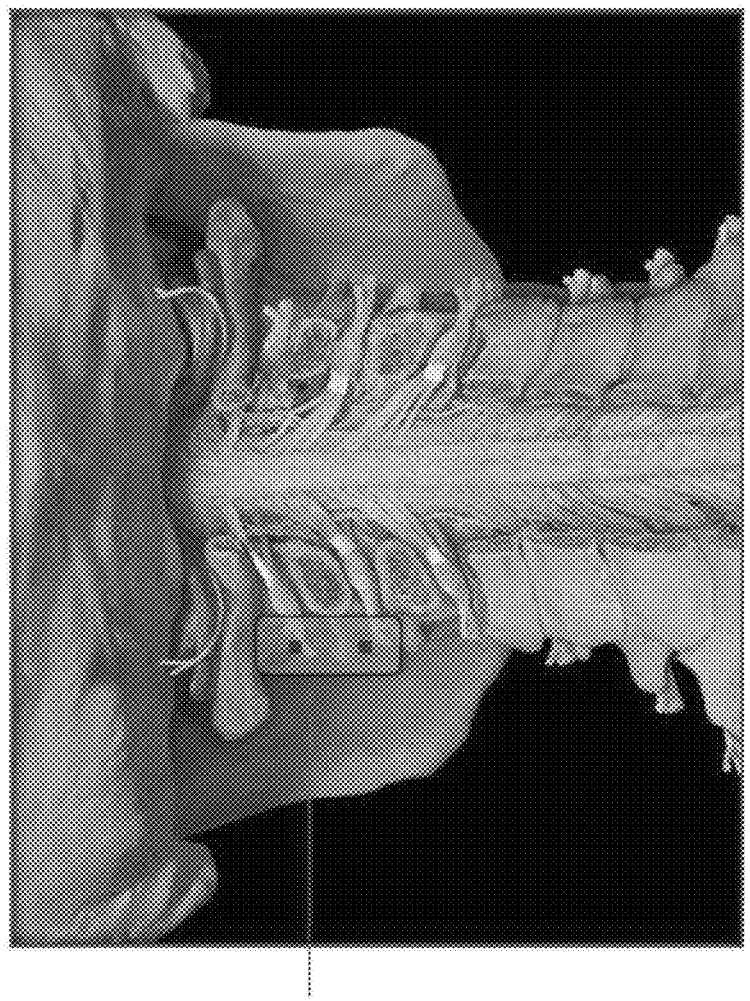
FIG. 3 illustrates a posterior view of spinal column, showing the location of a patch lead with respect to cervical nerve roots in accordance with an embodiment of the disclosure. Note that the patch is positioned lateral to the vertebral bone, at the exit point of the dorsal nerves from the spinal foramen, in the extraforaminal area in accordance with aspects of the disclosure.

More specifically, with reference to FIG. 3, in accordance with aspects of the disclosure, an extraforaminal electrical stimulation lead 300 may be implanted in a subdermal location in a target region of interest, e.g., on a patient's neck or upper back. The lead 300 may be positioned in proximity to one or more dorsal roots and DRGs. For instance, the lead may be positioned lateral to one or more vertebral bones, at the exit point of one or more dorsal nerves and above one or more dorsal roots and DRGs at the lateral exit point from the spinal foramen (i.e., the extraforaminal area). This subdermal location avoids possible damage to neural tissue that could occur with lead implantation into the cervical vertebral foramen or implantation of leads adjacent to the dorsal root or DRG.

In certain aspects of the disclosure, an implantable extraforaminal electrical stimulation system is provided including at least one extraforaminal electrical stimulation lead implantable at one or more extraforaminal areas in a target region of a patient, and a power source. During use, the lead is configured to drive an electrical current from the power source into targeted regions of the spinal cord of the patient, such as the dorsal root and DRG, to induce analgesia. In certain embodiments, the power source may be an implantable pulse generator (IPG) or an external pulse generator (EPG).

In certain aspects, an extraforaminal electrical stimulation lead of the disclosure may comprise at least one conductive electrode contact to provide electrical stimulation upon application of electrical current to the lead. In certain embodiments, the conductive electrode contacts may be positioned in at least one surface of a lead body formed of insulative material. In certain aspects, the conductive electrode contacts may be embedded within at least one surface an insulative lead body in a manner to provide unidirectional electrical stimulation to a target region upon application of electrical current to the lead, as described in further detail herein. Further, in certain embodiments, the conductive electrode contacts may be interconnected and/or connected to a power source, by one or more conductive members. In certain embodiments, the conductive members may be comprised of one or more conductive wires, as described in further detail herein. As described in further detail herein, the one or more conductive members may be at least partially positioned within the lead body formed of insulative material and/or comprise an electrically insulating coating.

Any conductive electrode contact, conductive member, and insulative material suitable for human physiological purposes may be used, as generally known in the art. For instance, conductive electrode contacts may be formed of a non-corrosive, highly conductive material. Non-limiting examples of such material include platinum and platinum alloys, such as platinum-iridium alloys.

In certain embodiments, the lead body may be formed of one or more layers of insulative material, which layers may be formed of the same or different insulative material. In certain embodiments, the conductive electrode contacts and conductive members may be positioned within a single layer of insulative material of the lead body, or may be positioned between layers of insulative materials of the lead body. The lead body (or layers of the lead body) may be formed from any insulative material suitable for implantation into the human body which is physiologically inert. By way of non-limiting example, polyurethane, polyethylene, or silicone rubber may be used.

The conductive member may be formed from any material that is electrically conductive, such as nickel-titanium, platinum, gold, silver, palladium, other noble metals, and other alloys or metals suitable for use in the human body. In certain embodiments, the conductive member may be positioned within the insulative lead body and/or may comprise an electrically insulating coating. By way of non-limiting example, the electrically insulting coating may be formed from a polyurethane, polyethylene, silicone rubber, or a flouro-polymer, such as ethyletetraflouroethylene or polytetrafluoroethylene (PTFE). In certain embodiments, the electrically insulating coating may have with a coating thickness of approximately 0.0005 inch. Further, in certain embodiments, the conductive member may be comprised of one or more wires. Each wire may have a diameter of between about 0.002 and about 0.006 inches. The number of conductor members may generally be determined by the number and configuration of electrode contacts, and the electrical signals to be generated, as recognized by those of skill in the art.

In one embodiment, the conductive electrode contacts may be configured as an electrode array with a single directionality to focus the stimulation. The single directionality may further reduce power consumption by the lead. In certain embodiments, the electrode array includes one or more electrode contacts arranged in a desired pattern to maximize programming potential for electrical stimulation. In certain embodiments, the electrode array pattern may be symmetrical about a center-line of the lead. In other embodiments, the electrode array may be asymmetrical along the lead, designed to focus stimulation to a specific anatomical formation.

In certain embodiments, the conductive electrode contacts may be arranged in various electrode array configurations with different dimensions. The electrode array configurations may include any number of electrode contacts, for example, one, two, four, six, eight, twelve, sixteen, or the like. Each of the electrode contacts may be sized and shaped in any manner known in the art. For instance, the electrode contacts may have a length ranging from approximately 1.5 mm to 4 mm. In some specific examples, the length of the electrode contacts may be approximately 1.5 mm, 2 mm, 2.5 mm, 3 mm, or 4 mm. The electrode contacts may further have a longitudinal spacing ranging from approximately 1 mm to 4 mm depending on the electrode array configuration. For example, the longitudinal spacing may be approximately 1 mm, 2 mm, 3 mm, 4 mm, or the like. The electrode array configuration may have an array length ranging from approximately 10 mm to 24 mm, again depending on the electrode array configuration.

In certain embodiments, the extraforaminal electrical stimulation lead may be a patch-type lead. By way of non-limiting example, the patch-type lead may be shaped as a flexible, rectangular or square patch. However, any suitable shape may be utilized, e.g., any shape suitable for use in the desired anatomical location with coverage to provide electrical stimulation to the desired anatomical region. For instance, the patch-type lead may have an tapered or narrowed distal and/or proximal end to facilitate placement in the small regions of the cervical and/or thoracic spine. The lead may formed from flexible materials as described herein, generally suitable for use in surgical implantation. For instance, the patch-type lead may be formed of flexible materials so as to be collapsible, to facilitate rolling and unrolling during minimally invasive surgical implantation procedure using an introducer and/or catheter system, as described herein.

In accordance with certain embodiments, the patch-type lead may have a thin, compact, low profile, shape to facilitate minimally invasive implantation as described herein. The lead may generally be of a suitable thickness for use in the implantation and extraforaminal stimulation of at least one dorsal root and DRG. It will be appreciated that the patch-type leads may have a variety of dimensions forming the thin, compact, low profile. For example, the patch-type may have a length of approximately 30 mm, 45 mm, 60 mm, 75 mm, 90 mm, or similar lengths. Further, the lead may typically range from about 0.030 inches to about 0.070 inches in thickness, in some embodiments 0.030 inches to 0.050 inches, as generally recognized by those of skill in the art.

In accordance with aspects of the disclosure, the lead may further be sized and shaped to facilitate navigating the spinal anatomy of a patient during implantation of the lead and once implanted, to provide a flexibility of lead during electrical stimulation.

Figure 4:
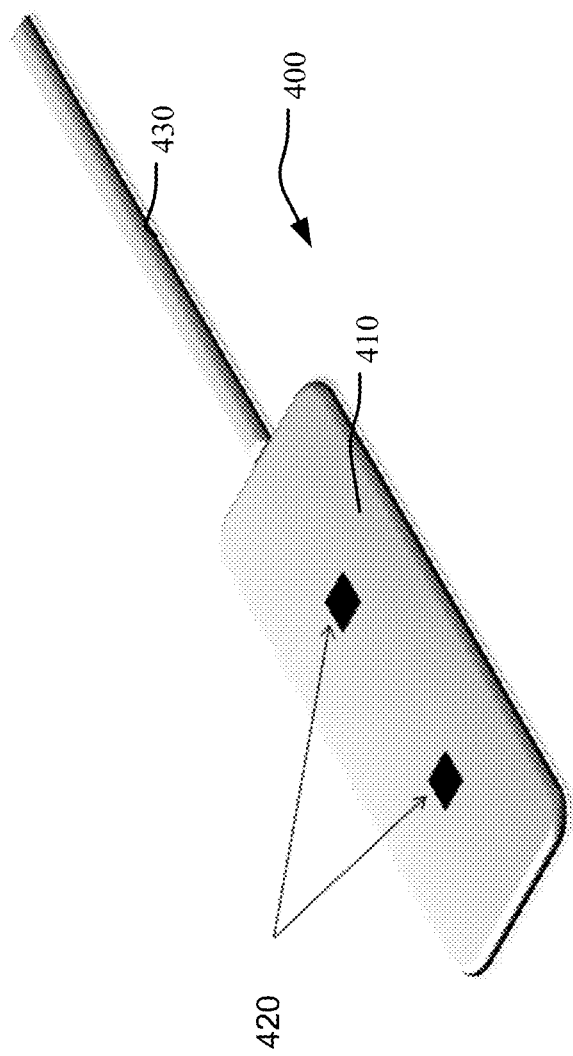
FIG. 4 is an isometric view of an exemplary patch lead in accordance with an embodiment of the disclosure.

In one embodiment, with reference to FIG. 4, a patch-type extraforaminal electrical stimulation lead is illustrated. The patch-type lead 400 may have two or more conductive electrode contacts 420 (e.g., Platinum iridium) embedded in a flexible, rectangular-shaped insulative body 410 (e.g., silicone rubber), with the electrode contacts 420 exposed on one side to deliver unidirectional electrical current towards the target region during use (e.g., dorsal roots and DRG). As illustrated, lead 400 includes two electrode contacts. However, as described herein, extraforaminal electrical stimulation leads of the disclosure may comprise more than two electrode contacts, e.g., formed as an array of electrode contacts to provide desired directionality of current, etc. The electrode contacts 420 are connected by conductive members, e.g., conductive wiring (not shown), which runs through body 410 and into an insulated cable 430, which in turn is connected to a power source (not shown, e.g., an IPG). In certain aspects, electrical current can be delivered between two or more electrode contacts, or between electrode contact(s) and the IPG can, which would serve as the anode.

Figure 5:
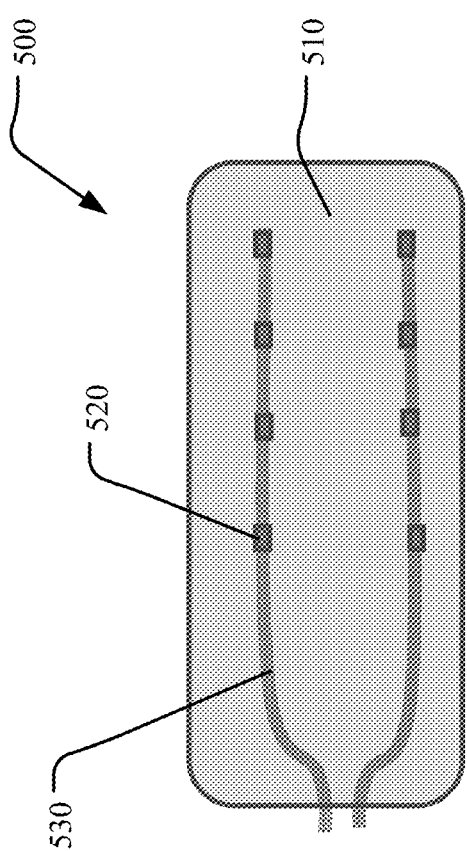
FIG. 5 illustrates a collapsible patch lead in accordance with an embodiment of the disclosure.

In another embodiment, with reference to FIG. 5, a collapsible patch-type extraforaminal electrical stimulation lead is illustrated. The patch-type lead 500 may have two or more conductive electrode contacts 520 that are aligned into columns on opposite sides of a midline of a flexible, collapsible lead body 510, with the electrode contacts 520 exposed on one side to deliver unidirectional electrical current towards the target region during use (e.g., dorsal roots and DRG). As illustrated, lead 500 includes eight electrode contacts. However, as described herein, extraforaminal electrical stimulation leads of the disclosure may comprise a variety of electrode contact count and configurations, e.g., formed as an array of electrode contacts to provide desired directionality of current, etc. The electrode contacts 520 are connected to conductive members 530, e.g., conducive wiring, which runs through collapsible lead body 510 and into insulated cabling (not shown), which in turn is connected to a power source (not shown, e.g., an IPG). In accordance with certain aspects of the disclosure, lead 500 may fold or collapse between the columns of electrode contacts 520 so that it be implanted using minimally invasive implantation methods described herein (e.g., via an introducer).

In other embodiments, the extraforaminal electrical stimulation lead may be comprised of a thin, flexible wire with insulated body and conductive tip. Any suitable size and shape of wire may be used for the intended purpose. For example, the diameter of the wire may be 1 F (0.33 mm). In such configuration, the lead may generally be positioned in the extraforaminal area with the conductive tip located in the target region where electrical stimulation is desired. A benefit of this wire lead design is that it can be implanted in a minimally-invasive fashion without the need for an introducer, as described in further detail herein.

Figure 6:
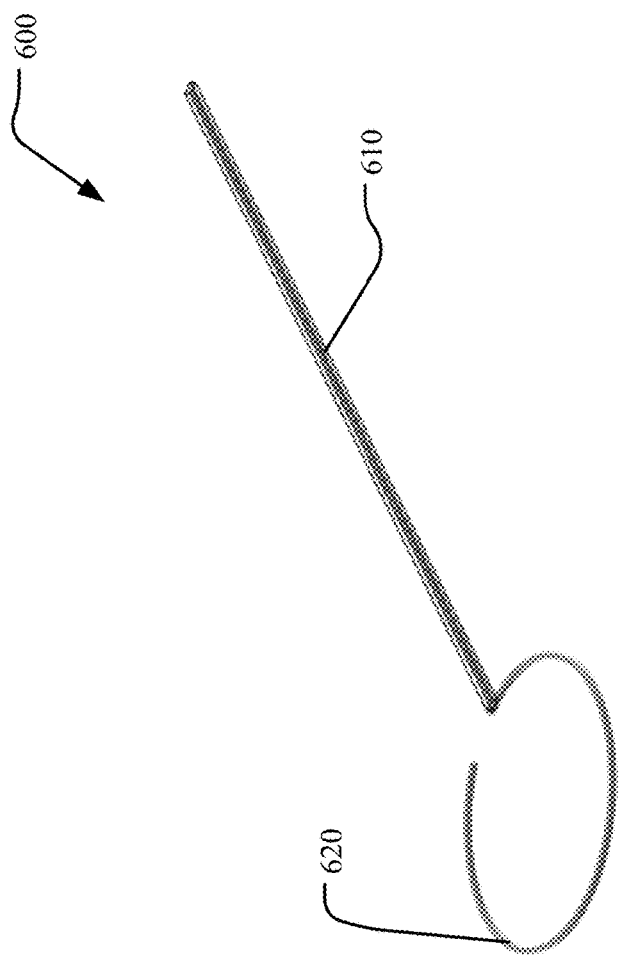
FIG. 6 illustrates a wire lead, with insulated body and conductive circular tip in accordance with an embodiment of the disclosure.

In certain embodiments, with reference to FIG. 6, the extraforaminal electrical stimulation lead 600 may be comprised of a thin, flexible wire with an insulted body 610 and a conductive tip 620, wherein the conductive tip may be circular to increase the surface area of the electrode contact. One or more wire leads may be implanted, and stimulation may be delivered between two or more wires (e.g., between the conductive tips of wire leads), or between wire lead(s) and a power source, e.g., IPG can.

In certain aspects of the disclosure, minimally invasive implantation methods are provided for implanting extraforaminal electrical stimulation leads described herein. In accordance with the minimally invasive implantation methods of the disclosure, the extraforaminal electrical stimulation lead is implanted through a small incision in the dermis of the patient and into the subcutaneous fat layer, between the skin and musculature. The lead is placed in at least one extraforaminal area of the spine in a target region in proximity of at least one dorsal root and DRG of a patient in need of spinal stimulation treatment.

By way of example, in certain embodiments, the extraforaminal electrical stimulation lead may be implanted using a minimally-invasive approach through a small incision near the target site. In some embodiments, the lead may optionally be sutured in place after implantation to anchor the lead in a desired anatomical location.

In certain embodiments, extraforaminal electrical stimulation lead may be positioned into place in the extraforaminal area via an introducer (e.g., a catheter system). In some embodiments, the introducer may comprise a lumen and sheath. The introducer may be inserted into the extraforaminal area of the target region of the spine of the patient using a catheter system. By way of example, the lead may be positioned in the extraforaminal area in any suitable manner, such as by inserting the lead into lumen of the introducer; inserting the introducer having the lead within its lumen through the incision into the desired location of the extraforaminal area of the target region of the spine of the patient; pushing the lead out of the lumen of the introducer into the desired location of the extraforaminal area; and removing the sheath of the introducer from the patient through the incision, thereby leaving the lead in the desired location of the extraforaminal area.

Figure 7:
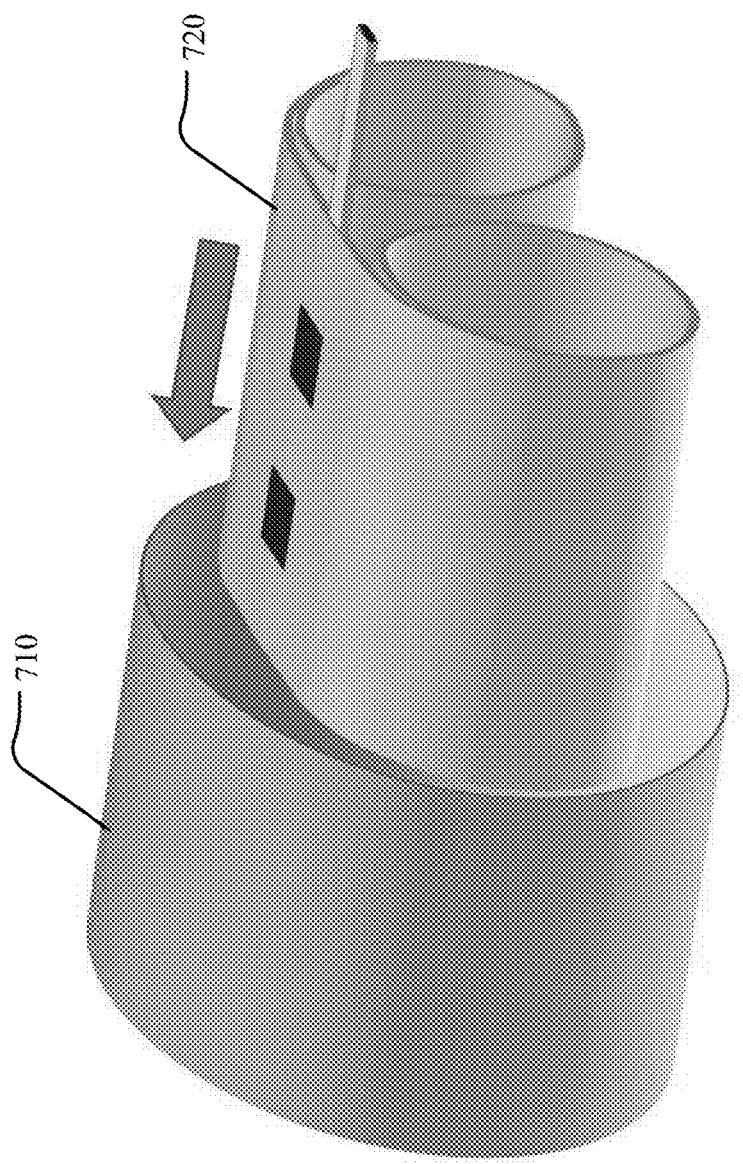
FIG. 7 illustrates a rolled patch lead being inserted into an introducer in accordance with an embodiment of the disclosure.

In accordance with certain aspects of the disclosure, with reference to FIG. 7, an extraforaminal electrical stimulation lead 720 may be implanted using a minimally invasive approach via an introducer 710 (catheter). In certain embodiments, a thin, flexible extraforaminal electrical stimulation lead 720 can be rolled up such that it will fit through the circular opening of the introducer 710. The introducer 710 may then inserted through a small incision in the skin, and at the appropriate location, the lead 720 may be pushed out of the introducer 710 and into the subdermal space.

If necessary, a tool may first be used to open up the subdermal space for the lead. Upon exiting the introducer, the lead naturally unrolls so that it lies flat. The large surface area of the lead helps to hold the lead in the same location over time, even with changes in patient posture. Moreover, the lead can be anchored by suturing it to the skin or musculature. The lead may have suture holes along the border of the insulation material to facilitate suturing.

In another embodiment, the extraforaminal electrical stimulation may be directly implanted through a small incision into the extraforaminal area without an introducer.

In accordance with aspects of the disclosure, methods of providing extraforaminal electrical stimulation to a patient in need thereof are provided. In certain embodiments, the method comprises delivering electrical current from at least one electrical stimulation lead of the disclosure, implanted in an extraforaminal area of the spine of a patient in proximity to at least dorsal root and dorsal root ganglion in a target region of the patient to thereby provide paresthesia to the patient. In certain embodiments, the electrical current is delivered from at least one extraforaminal electrical stimulation lead described herein, unidirectionally through the musculature and into at least one targeted dorsal roots and DRG. In certain embodiments, the one extraforaminal electrical stimulation lead is implanted subdermally, as described herein.

In accordance with certain embodiments of the disclosure, stimulation is delivered to target the cervical dorsal roots and DRG as they exit the foramen. In certain aspects, the systems, leads, and methods of the disclosure may be used to treat chronic pain of the neck or upper limbs, with the targeted dorsal roots and DRG corresponding to the painful body dermatomes.

In certain embodiments, to avoid generating muscle contractions and to increase the threshold difference for nerve and muscle activation, a stimulation waveform with short pulse width may be applied (e.g., less than or equal to about 100 μs). Additionally, use of high frequency stimulation (e.g., greater than or equal to about 100 Hz) may reduce discomfort associated with muscle contractions. The dorsal root(s) and DRG targeted for stimulation will generally correspond to a given patient's painful body dermatome areas in the neck or upper limbs. In certain embodiments, multiple locations may be targeted with a single lead, depending on the span of the lead, number of electrode contacts, and position of electrode contacts, as described in further detail herein. In other embodiments, multiple leads may be implanted and used to target multiple locations.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed:

1. A method of providing extraforaminal electrical stimulation to at least one dorsal root and dorsal root ganglion to provide analgesia to a patient in need thereof, the method comprising:

delivering electrical current from at least one electrical stimulation lead implanted in an extraforaminal area of the spine of a patient in proximity to at least dorsal root and dorsal root ganglion in a target region of the patient to thereby provide analgesia to the patient, wherein the electrical current is delivered unidirectional through the musculature of the patient into the dorsal root and dorsal root ganglion.

2. The method of claim 1, wherein the at least one electrical stimulation lead is implanted subdermally in the extraforaminal area.

3. The method of claim 1, wherein the at least one electrical stimulation lead is implanted in the cervical and/or thoracic spine of the patient.

4. The method of claim 1, wherein the electrical current is delivered using a stimulation waveform with short pulse width of less than or equal to about 100 µs.

5. The method of claim 1, wherein the electrical current is delivered using a high frequency stimulation of greater than or equal to about 100 Hz.

6. A method of providing extraforaminal electrical stimulation to at least one dorsal root and dorsal root ganglion to provide analgesia to a patient in need thereof, the method comprising:

delivering electrical current from at least one electrical stimulation lead implanted in an extraforaminal area of the spine of a patient in proximity to at least dorsal root and dorsal root ganglion in a target region of the patient to thereby provide analgesia to the patient, wherein the electrical current is provided from a patch-type lead sized and shaped so as to facilitate implantation in at least one extraforaminal area in proximity to at least one dorsal root and dorsal root ganglion.

7. The method of claim 1, wherein the electrical current is provided from an extraforaminal electrical stimulation lead comprised of a thin, flexible wire with insulated body and conductive tip.

8. A method of providing extraforaminal electrical stimulation to at least one dorsal root and dorsal root ganglion to provide analgesia to a patient in need thereof, the method comprising:

delivering electrical current from at least one electrical stimulation lead implanted in an extraforaminal area of the spine of a patient in proximity to at least dorsal root and dorsal root ganglion in a target region of the patient to thereby provide analgesia to the patient, wherein:

the electrical current is provided from an extraforaminal electrical stimulation lead comprised of a thin, flexible wire with insulated body and conductive tip, and the conductive tip is comprised of circular shape.

9. A minimally invasive method for implanting an electrical stimulation lead into an extraforaminal area of a patient in need of spinal electrical stimulation treatment, the method comprising:

providing a small incision through the dermis of a patient near a target region of the spine of a patient for placement of an extraforaminal electrical stimulation lead;

using an introducer to implant an extraforaminal electrical stimulation lead in the subcutaneous fat layer of the patient, between the skin and musculature, in an extraforaminal area of the target region of the spine of the patient in proximity of at least one dorsal root and dorsal root ganglion, wherein the using the introducer to implant the extraforaminal stimulation lead into the extraforaminal area comprises:

inserting the lead into a lumen of the introducer, wherein the lead is rolled upon insertion into the lumen of the introducer;

inserting the introducer having the lead within its lumen through the incision into the desired location of the extraforaminal area of the target region area of the spine of the patient;

pushing the lead out of the lumen of the introducer into the desired location of the extraforaminal area, wherein the lead unrolls upon being pushed from the lumen of the introducer into the extraforaminal area such that the lead lies flat and is positioned in proximity to at least one dorsal root and dorsal root ganglion to provide unidirectional electrical stimulation upon delivery of electrical current during use; and removing a sheath of the introducer from the patient through the incision, thereby leaving the lead in the desired location of the extraforaminal area; and optionally suturing the extraforaminal electrical stimulation lead to anchor the lead in place.

10. The method of claim 6, wherein the electrical current is delivered unidirectional through the musculature of the patient into the at least one dorsal root and dorsal root ganglion.

11. The method of claim 6, wherein: the electrical current is provided from an extraforaminal electrical stimulation lead comprised of a thin, flexible wire with insulated body and conductive tip, and the conductive tip is comprised of circular shape.

12. The method of claim 11, wherein the electrical current is delivered unidirectional through the musculature of the patient into the at least one dorsal root and dorsal root ganglion.

13. The method of claim 6, wherein the at least one electrical stimulation lead is implanted subdermally in the extraforaminal area.

14. The method of claim 6, wherein the at least one electrical stimulation lead is implanted in the cervical and/or thoracic spine of the patient.

15. The method of claim 6, wherein the electrical current is delivered using a stimulation waveform with short pulse width of less than or equal to about 100 µs.

16. The method of claim 6, wherein the electrical current is delivered using a high frequency stimulation of greater than or equal to about 100 Hz.

17. The method of claim 8, wherein the electrical current is delivered unidirectional through the musculature of the patient into the dorsal root and dorsal root ganglion.

18. The method of claim 8, wherein the at least one electrical stimulation lead is implanted subdermally in the extraforaminal area.

19. The method of claim 8, wherein the electrical current is delivered using a stimulation waveform with short pulse width of less than or equal to about 100 µs.

20. The method of claim 8, wherein the electrical current is delivered using a high frequency stimulation of greater than or equal to about 100 Hz.

* * * * *